United States Patent [19]

Makisumi et al.

[11] 4,256,899

[45] Mar. 17, 1981

[54] PROCESS FOR THE PRODUCTION OF 3-AMINO-5-T-BUTYLISOXAZOLE

[75] Inventors: Yasuo Makisumi, Kawanishi; Akira Murabayashi, Ibaraki; Akira Takase, Kobe; Ichiro Ishizuka; Shinzaburo Sumimoto, both of Osaka, all of Japan

[73] Assignee: Shionogi & Co., Ltd., Osaka, Japan

[21] Appl. No.: 82,405

[22] Filed: Oct. 5, 1979

[30] Foreign Application Priority Data

Oct. 12, 1978 [JP] Japan ................................ 53-125980

[51] Int. Cl.³ ........................................... C07D 261/14
[52] U.S. Cl. .................................................... 548/246
[58] Field of Search ......................................... 548/246

[56] References Cited

U.S. PATENT DOCUMENTS 4,152,336   5/1979   Kuroki et al. ......................... 548/246

*Primary Examiner*—Anton H. Sutto
*Attorney, Agent, or Firm*—Wenderoth, Lind & Ponack

[57] ABSTRACT

3-Amino-5-t-butylisoxazole is prepared by reacting pivaloylacetonitrile with hydroxylamine in aqueous medium under basic conditions and treating the reaction products with an acid. The process is economical and industrial.

8 Claims, No Drawings

PROCESS FOR THE PRODUCTION OF 3-AMINO-5-T-BUTYLISOXAZOLE

The present invention relates to a process for the production of 3-amino-5-t-butylisoxazole.

3-Amino-5-t-butylisoxazole is a synthetic intermediate for 1,1-dimethyl-3-(5-t-butyl-3-isoxazolyl)urea (generic name, Isouron) useful as a selective herbicide for sugar cane and other plants [Yukinaga, et al., U.S. Pat. Nos. 4,062,861; 4,111,680]. Makisumi et al. have developed a process for preparing 3-amino-5-t-butylisoxazole in high yield which comprises reacting pivaloylacetonitrile with methanol/dry hydrogen chloride to give an intermediary iminoether and reacting the latter with hydroxylamine in the presence of a base [Makisumi et al., Japanese Patent Appln. No. 68173/1977] (hereinafter referred to as "iminoether route"). This process, however, has several defects including slightly troublesome operations and requirement of non-aqueous reaction phase in the former step. The present invention has been established by solving such technical problems.

Accordingly, the present invention is directed to an economical process for the production of 3-amino-5-t-butylisoxazole which comprises reacting pivaloylacetonitrile with hydroxylamine in aqueous medium under basic conditions and treating the reaction products with an acid. The process of this invention is illustrated by the following scheme:

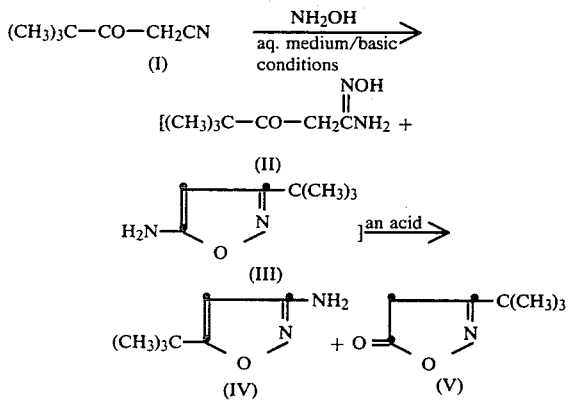

The aqueous medium includes water and hydrous alcohols such as hydrous methanol or hydrous ethanol. Weak basicity of pH 7.0–9.0, in particular around pH 8.0, is preferred for the basic conditions. The base includes an inorganic alkali such as alkali hydroxide (e.g. sodium hydroxide, potassium hydroxide, lithium hydroxide), alkali carbonate (e.g. sodium carbonate, potassium carbonate), or alkali hydrogen carbonate (e.g. sodium hydrogen carbonate, potassium hydrogen carbonate), an organic amine such as triethylamine or tributylamine, and ammonia. For the acid treatment an inorganic acid is used such as hydrochloric acid, sulfuric acid, nitric acid, or hydrobromic acid. Both the former and latter steps are carried out by heating at room temperature to 150° C., preferably at about 50 to 100° C. The acid treatment has an object to convert the intermediary oxime (II) into the final product (IV) via the ring closure and hydrolyze the 5-amino compound, isomer of IV, to 3-t-butyl-5-isoxazolone (V).

Amount of hydroxylamine to the starting material (I) is 1.0 to 1.2 mol equivalent, preferably about 1.1 mole equivalent. Amount of a base is an amount necessary to neutralize a hydroxylamine salt, or a slight excess thereof, and may be adjusted so as to afford a prescribed pH value, in the range of 0.5 to 2.0 mol equivalent. Amount of an acid used in the latter step is 0.3 to 0.5 mol equivalent in excess of the amount which would be enough to neutralize the reaction mixture. The oxime (II) in the former step, as crystals melting at 100.0° to 100.5° C., may optionally be isolated and then subjected to the latter acid treatment, but the latter step is ordinarily carried out by adding an acid to the reaction mixture containing II.

Industrial advantages of the present invention are illustrated below:

(a) Since the reaction in the present invention proceeds in aqueous medium, commercially available aqueous hydroxylamine sulfate solution can be utilized.

(b) Operations in the present invention are simpler than the iminoether route and so the iminoether formation step of the starting pivaloylacetonitrile (I) can be avoided.

(c) The product (IV) is prepared in high yield.

(d) A by-product, 3-t-butyl-5-aminoisoxazole (III) is easily hydrolyzed into 3-t-butyl-5-isoxazolone (V) (an acidic material) by the acid treatment, which can be easily removed. Thus, the final product (IV) is obtained in high purity.

(e) A solvent such as chloroform, benzene or toluene is suitable for extracting the product (IV). In particular, use of toluene is preferable, because the product (IV) is continuously converted into Isouron (VII) (as described below) and the like without isolation of IV in the form of crystals.

(f) It is not necessarily required to use the starting material (I) in the form of crystals. The pivaloylacetonitrile (I) is ordinarily prepared as a solution of I in a solvent such as benzene or toluene but may be also available as an aqueous solution of alkali metal salt of I by keeping a small amount of solvent after evaporation of the above solution and dissolving the residue in an aqueous solution of an appropriate alkali hydroxide.

(g) Another by-product, 3-(3-t-butyl-5-isoxazolyl)-amino-5-t-butylisoxazole (VI) (described below) can be hydrolyzed with an acid such as hydrochloric acid or sulfuric acid under heating to give 3-amino-5-t-butylisoxazole (IV) and 3-t-butyl-5-isoxazolone (V), whereby the yield and purity of the product (IV) can be raised. This is shown by the following scheme:

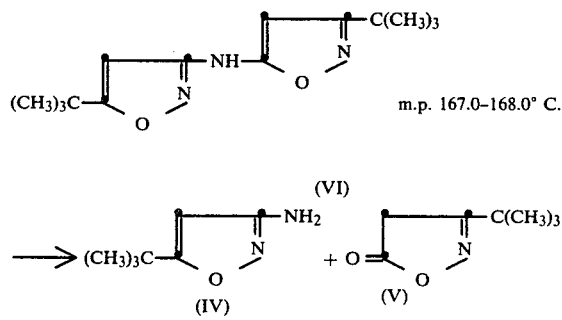

Conversion of the product (IV) to Isouron (VII) is illustratively shown below:

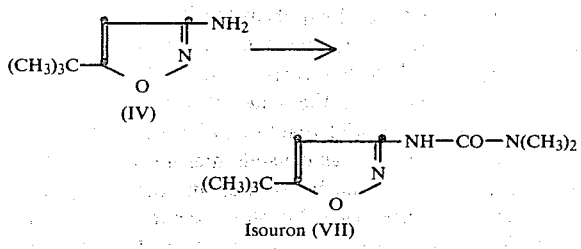

Isouron (VII)

(1) Reaction of IV with dimethylcarbamoyl chloride in the presence of Lewis acid such as aluminum chloride (Japanese Patent Appln. No. 49629/1977).

(2) Formation of hydrochloride of IV, followed by reaction of the hydrochloride with phosgene in toluene and reaction of the resulting product with dimethylamine (Japanese Patent Unexamined Publications Nos. 63170/1976; 75064/1976).

Presently-preferred and practical embodiments of the present invention are illustratively shown in the following examples.

EXAMPLE 1

In a mixture of pivaloylacetonitrile (25.03 g) and 50% (v/v) ethanol (400 ml) is dissolved 96% sodium hydroxide (9.583 g). To this solution is added hydroxylamine hydrochloride (purity, 96%) at 27° C. to give a solution (pH 7.8), which is stirred at 60° C. for 22 hours. The reaction mixture is cooled at 20° C., mixed with conc. hydrochloric acid (9.11 g), and stirred at 50° C. for 2 hours. Conc. hydrochloric acid (14.18 g) is added to the mixture, which is refluxed at 100° C. for 1 hour. The reaction mixture is concentrated under reduced pressure to remove ethanol and the residue is mixed with 30% sodium hydroxide (62 g). The mixture is shaken with chloroform. The chloroform layer is washed with water, dried over anhydrous sodium sulfate and concentrated under reduced pressure to give 3-amino-5-t-butylisoxazole (23.76 g). Yield, 84.74%. m.p. 101–109.5° C. Purity, 95.1%. The alkaline washings give 3-t-butyl-5-isoxazolone (2.60 g; yield, 9.21%).

EXAMPLE 2

To a suspension of pivaloylacetonitrile (25.03 g) in water (400 ml) is added 96% sodium hydroxide (9.17 g). Hydroxylamine sulfate (18.06 g) is added to the resulting solution at 27° C. The mixture is stirred at room temperature for 30 minutes, adjusted to pH 8 with 10% sulfuric acid (0.97 g), stirred at 60° C. for 22 hours, cooled at 20° C., mixed with conc. hydrochloric acid (7.90 g), and heated at 50° C. for 2 hours. Conc. hydrochloric acid (14.18 g) is added to the mixture, which is heated at 100° C. for 1 hour. After cooling, the reaction mixture is adjusted to pH 11 with 30% sodium hydroxide (49.8 g) and shaken with chloroform. The organic layer is washed with water, dried over anhydrous sodium sulfate and concentrated to remove chloroform, whereby 3-amino-5-t-butylisoxazole (24.16 g) is obtained. Yield, 86.2%. Purity, 95.4%. m.p. 103.5–109° C.

The mother liquor after extraction is mixed with the washings, adjusted to pH 1 with conc. hydrochloric acid and extracted with benzene. The organic layer is treated in a conventional manner to give 3-t-butyl-5-isoxazolone (2.48 g; yield, 8.8%).

EXAMPLE 3

A suspension of pivaloylacetonitrile (12.52 g), sodium carbonate (8.74 g) and water (200 ml) is stirred and mixed with hydroxylamine sulfate (9.03 g) at 25° C. pH 7.11. The reaction mixture is treated as in Example 2 to give 3-amino-5-t-butylisoxazole (12.01 g). Yield, 85.7%. Purity, 95.8%.

The mother liquor after extraction gives 3-t-butyl-5-isoxazolone (1.42 g; yield, 10.1%).

EXAMPLE 4

A suspension of pivaloylacetonitrile (12.52 g) and triethylamine (11.27 g) in water (200 ml) is stirred and mixed with hydroxylamine sulfate (9.03 g). pH 8.22. The reaction mixture is treated as in Example 2 to give 3-amino-5-t-butylisoxazole (11.45 g; yield, 81.7%).

The mother liquor after extraction gives 3-t-butyl-5-isoxazolone (1.72 g; yield, 12.2%).

EXAMPLE 5

To a suspension of pivaloylacetonitrile (1.252 g) and 86% potassium hydroxide (0.717 g) in water (20 ml) is added hydroxylamine sulfate (0.903 g) at 25° C. and the mixture is stirred for 3 minutes. pH 8.30. The reaction mixture is treated as in Example 2 to give 3-amino-5-t-butylisoxazole (1.204 g). Yield, 85.9%. Purity, 95.8%.

The mother liquor after extraction gives 3-t-butyl-5-isoxazolone (0.153 g; yield, 10.8%).

EXAMPLES 6–8

Using the bases shown below, the reactions are carried out as in Example 2, whereby the product (IV) and the by-product (V) are obtained as shown in the following table:

| Ex. No. | Base Sort | Mol equivalent to I | pH | Conc. HCl Mol equivalent to I | IV Yield (%) | IV Purity (%) | V Yield (%) |
| --- | --- | --- | --- | --- | --- | --- | --- |
| 6 | LiOH . H$_2$O | 1.1 | 7.90 | 1.3 | 82.1 | 94.7 | 12.7 |
| 7 | K$_2$CO$_3$ | 0.75 | 7.10 | 1.6 | 87.0 | 94.5 | 10.8 |
| 8 | NaHCO$_3$ | 1.5 | 6.98 | 1.6 | 83.8 | 92.3 | 13.2 |

EXAMPLE 9

To a solution of pivaloylacetonitrile (25.03 g) and 48% sodium hydroxide (18.16 g) in water (319 ml) is added a solution of hydroxylamine sulfate (18.06 g) in water (72 ml) and the mixture is adjusted to pH 8.10±0.05 with 5% sodium hydroxide (0.38 g), stirred at 60° C. for 18 hours, mixed with 36% hydrochloric acid (26.13 g) and stirred at 70° C. for 30 minutes. Then, 36% hydrochloric acid (40.31 g) is added to the reaction mixture, which is refluxed for 40 minutes under stirring. The mixture is evaporated under atmospheric pressure to recover pinacolone (1.07 g; yield, 5.3%) and cooled to ordinary temperature. After cooling, the reaction mixture is adjusted to pH 11.8 with 48% sodium hydroxide (58.08 g) and shaken with chloroform. The chloroform layer is washed with water and concentrated under reduced pressure to give 3-amino-5-t-butylisoxazole (23.80 g). Purity, 96.6%. Yield, 84.9%. No by-product, 3-(3-t-butyl-5-isoxazolyl)amino-5-t-butylisoxazole, is detected.

The mother liquor after extraction is combined with aqueous washings, adjusted to pH 2.00 with 36% hydrochloric acid (9.63 g) and shaken with chloroform. The chloroform layer is evaporated to give 3-t-butyl-5-isoxazolone (1.6 g; yield, 5.7%).

What is claimed is:

1. Process for preparing 3-amino-5-t-butylisoxazole which comprises reacting pivaloylacetonitrile with hydroxylamine in an aqueous medium at pH 7.0–9.0, and treating the reaction products with an acid selected from the group consisting of hydrochloric acid, sulfuric acid, nitric acid and hydrobromic acid in an amount of 0.3–0.5 mol equivalent in excess of the amount which would be enough to neutralize the reaction mixture.

2. Process according to claim 1, in which hydroxylamine hydrochloride or hydroxylamine sulfate is used as the hydroxylamine.

3. Process according to claim 1, in which both the former and latter steps are carried out at room temperature to 150° C.

4. Process according to claim 3, in which both the former and latter steps are carried out at 50° to 100° C.

5. Process according to claim 4, in which the former step is carried out around 60° C.

6. Process according to claim 4, in which the latter step is carried out around the reflux temperature of the aqueous medium.

7. Process according to claim 2, in which hydroxylamine sulfate is used.

8. Process according to claim 1, in which conc. hydrochloric acid is used as the acid.

* * * * *